US008671494B2

(12) United States Patent
Headstrom

(10) Patent No.: US 8,671,494 B2
(45) Date of Patent: Mar. 18, 2014

(54) LOW FRICTION ROTATIONAL OR TRANSLATIONAL INTERFACE FOR A MECHANICAL SYSTEM

(75) Inventor: Patrick A. Headstrom, Seattle, WA (US)

(73) Assignee: Koninklijke Philips N.V., Eindhoven (NL)

(*) Notice: Subject to any disclaimer, the term of this patent is extended or adjusted under 35 U.S.C. 154(b) by 0 days.

(21) Appl. No.: 13/502,501

(22) PCT Filed: Oct. 15, 2010

(86) PCT No.: PCT/IB2010/054692
§ 371 (c)(1),
(2), (4) Date: Apr. 17, 2012

(87) PCT Pub. No.: WO2011/058465
PCT Pub. Date: May 19, 2011

(65) Prior Publication Data

US 2012/0216635 A1 Aug. 30, 2012

Related U.S. Application Data

(60) Provisional application No. 61/261,397, filed on Nov. 16, 2009.

(51) Int. Cl.
*A46B 13/02* (2006.01)

(52) U.S. Cl.
USPC .................................. 15/22.1; 15/22.4; 74/25

(58) Field of Classification Search
USPC .............................. 15/22.1, 22.2, 22.4; 74/25
See application file for complete search history.

(56) References Cited

U.S. PATENT DOCUMENTS

| | | | |
|---|---|---|---|
| 6,419,211 | B1 | 7/2002 | Hvittfeldt et al. |
| 2005/0005453 | A1 | 1/2005 | Egeresi |

FOREIGN PATENT DOCUMENTS

| | | | | |
|---|---|---|---|---|
| DE | 2236276 | A1 | | 2/1973 |
| DE | 202005003515 | U1 | | 7/2005 |
| JP | 2-52691 | | * | 2/1990 |
| WO | 2009027660 | A2 | | 3/2009 |

* cited by examiner

*Primary Examiner* — Randall Chin

(57) ABSTRACT

The mechanical system includes an interface for moving parts, with the mechanical system including a driving assembly and a driven assembly, wherein the driving assembly mates with the driven assembly at a mechanical joint (41). The driving assembly includes a rotating disc (16) and a drive arm (18) rotatably connected thereto. The driven assembly includes a pivot arm (40) which is driven by the drive arm and also a grounded member (44) fixed to the handle about which the pivot arm moves. A preload assembly, which includes a spring or springs (54, 56) is connected to the drive arm and the pivot arm so as to place a preload at the axis of rotation of the mechanical joint between the drive arm and the pivot arm.

13 Claims, 2 Drawing Sheets

LOW FRICTION ROTATIONAL OR TRANSLATIONAL INTERFACE FOR A MECHANICAL SYSTEM

This invention relates generally to a low-friction joint for an articulating (moving) arm in a mechanical system such as a power toothbrush.

Mechanical systems which include an articulating arm or arms, such as found in drive trains in power toothbrushes and other personal care appliances, have joints which permit non-continuous rotating action. With these joints there are often high friction losses, as well as added noise. Some of these joints use sleeve bearings or ball bearings to reduce friction losses, by providing a pivoting or rolling interface instead of a sliding interface. However, even these bearings typically have some friction losses as well as lost motion during operation of the appliance. This results in inefficient operation and in some cases increased power requirements to achieve desired results, such as effective cleaning of the teeth.

Accordingly, the mechanical system for a personal care appliance, which includes an interface between moving parts therein, comprises: a driving assembly; a driven assembly which includes a workpiece assembly for use in a personal care appliance; and a mechanical joint connecting the driving assembly to the driven assembly, including a preload assembly providing a preload force on the joint through the axis of rotation of the joint.

Figure 1:
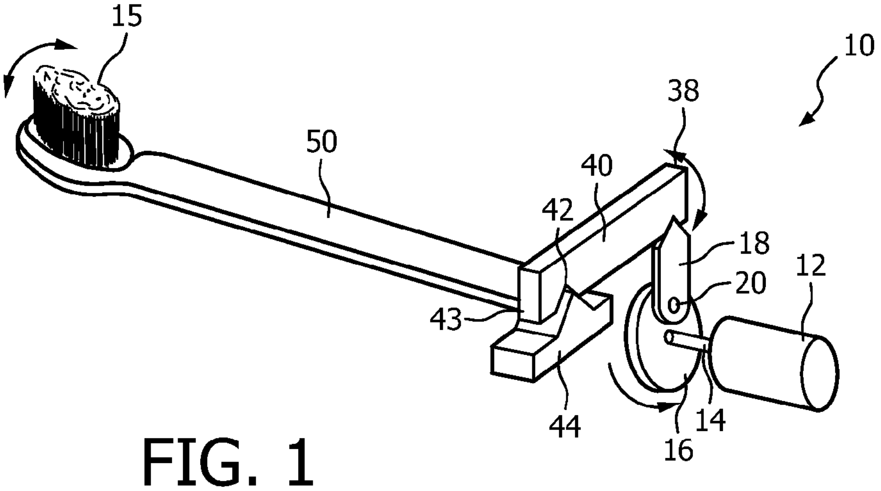
FIG. 1 is a simplified perspective view of a mechanical system for a personal care appliance, in particular a power toothbrush with a low-friction rotational interface described herein.
Figure 2:
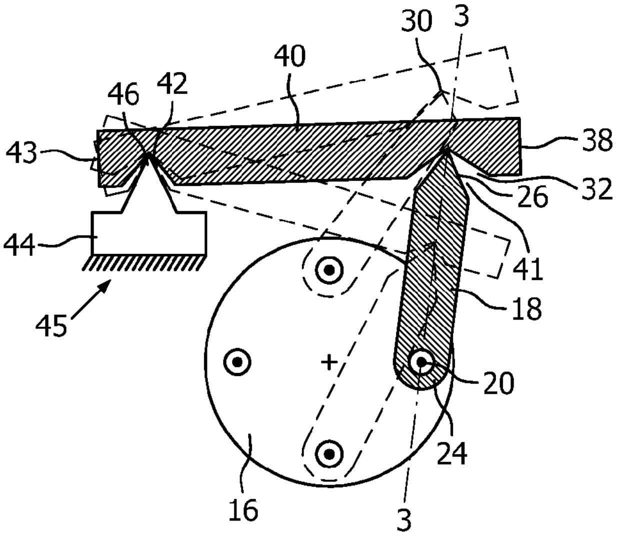
FIG. 2 is a side elevational view of a portion of FIG. 1.
Figure 3:
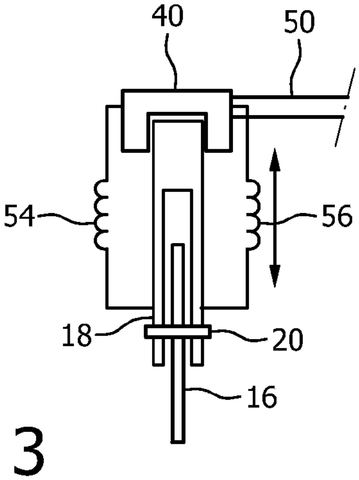
FIG. 3 is a cross-sectional view taken along lines 3-3 in FIG. 2.

FIGS. 1-3 show one embodiment of the mechanical interface arrangement of the present invention in a drive train portion of a hand held personal care appliance. FIG. 1 is a perspective view of such a mechanical interface in a drive train for a power toothbrush. However, it should be understood that the mechanical interface can be used in other healthcare devices, such as shavers or beard trimmers, for example. The toothbrush of FIG. 1, shown generally at 10, includes a conventional DC motor 12 having an output shaft 14, which runs in the range of 3000-18,000 rpm, to produce the desired output frequency of the workpiece 15. Attached to output shaft 14 is a disc 16 which rotates therewith. In the embodiment shown, disc 16 is made of metal or plastic, with a diameter of approximately 15mm, although this can be varied.

Attached to disc 16 is a pivot drive member 18 which is connected to disc 16 by a pin 20. Pivot drive member 18 is rotatably pinned to disc 16 near a lower end 24 of member 18 and is free to rotate about pin 20 as disc 16 rotates. Tip 26 of pivot drive member 18 narrows to a knife edge, as shown most clearly in FIG. 2. Tip 26 makes contact with the apex 30 of triangular slot 32, referred to as joint 41, in the vicinity of one end 38 of a pivot arm 40.

Pivot arm 40 in the embodiment shown is approximately 25 mm long by 6 mm wide and is made of either plastic or metal. Near the other end 43 of pivot arm 40 is another triangular slot 42 into which is fitted a pivot member 44 which is fixed to ground 45, such as the handle of the appliance. Pivot member

44 narrows to a knife edge tip 46 at the top end thereof, which fits into the apex of triangular slot 42.

In operation, as disc 16 rotates, pivot drive member 18 rotates about pin 20, which results in an arcuate movement of one end 38 of pivot arm 40 about fixed pivot member 44. As seen most clearly in FIG. 1, this results in an angular movement of brush arm 50 about its longitudinal axis with brush arm 50 connected at one end to and extending outwardly from end 43 of pivot arm 40. Brushhead 15 at the end of brush arm 50 also moves angularly about the longitudinal axis of the brush arm 50. In the embodiment shown, this angular movement is within the range of ±15° about a neutral position, although this can be varied to accommodate a particular applicator. In some cases, an angle of ±8° is preferred.

A significant feature of the arrangement of FIGS. 1-3 is a preload force which is applied between pivot drive member 18 and pivot arm 40. The pivot drive member 18 and the pivot arm 40 are held together with a preload force of approximately 3N by two springs 54 and 56 (FIG. 3) which are mounted along the axis of pivot drive member 18, i.e. through the center (axis) of rotation between the pivot drive member 18 and the pivot arm 40. In particular, springs 54, 56 are connected to the pivot drive member near the lower end thereof and to the pivot arm adjacent to the point of contact between the knife tip 26 of the pivot drive member and the apex of slot 32 in the pivot arm. The preload force at this pivot point or axis of rotation imparts no torque due to the rotating parts, resulting in a low friction interface between the two moving parts and resulting in very little or no play between the two moving parts as they move though an angular motion. This results in a savings of energy and a more efficient drive system and further produces less noise. Although FIG. 1 shows two springs 54 and 56, it is possible to use a single spring which extends through the axis of rotation.

Although the embodiment shown is directed toward a pivot (knife edge) contact arrangement, it should be understood that other contact configurations could be used, including generally a rolling type of contact using a ball, in which the two mating parts roll on each other.

Figure 4:
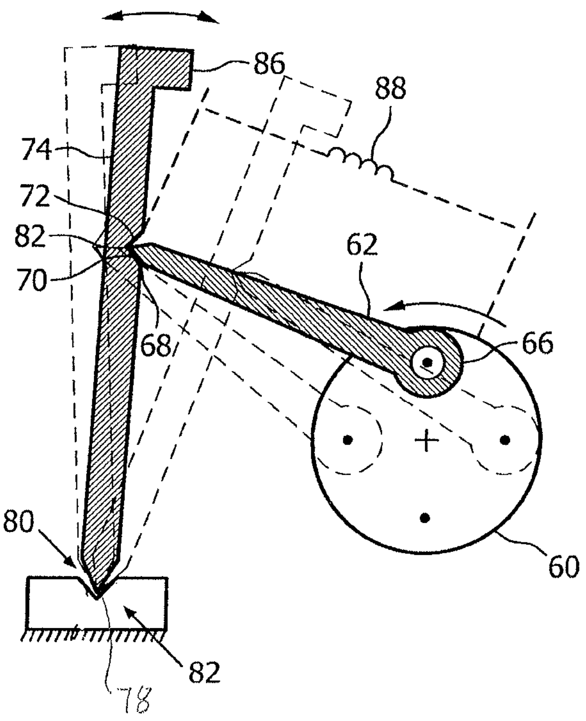
FIG. 4 is an elevational view of a mechanical system for an appliance with a low friction interface with translating workpiece motion.

FIG. 4 shows a second embodiment, involving an arrangement which results in a translational motion of the workpiece. This embodiment also includes a rotating disc 60 which is driven by a conventional DC motor (not shown). Rotatably attached to the disc is one end of a pivot drive member 62, connected by pin 66. The other end 68 of the pivot drive member terminates in a knife edge 70, which engages the apex of slot 72 in a pivot arm 74, which is arranged so as to pivot about a generally vertical position. The lower end of pivot arm 74 is a contact knife edge tip 78 which fits into a slot 80 of a pivot member 82 which is fixed to ground, i.e. the handle of the appliance. At the other upper end of pivot arm 74 is mounted a workpiece member 86, such as a brushhead.

In operation, rotation of disc 60 by motor action results in a generally translational, but also somewhat arcuate movement of pivot arm 74 about contact knife edge tip 78, through an angle typically within the range of ±8° . Similar to the embodiment of FIGS. 1-3, spring members 88 (shown moved away from actual connections for clarity) connect the pinned end of drive member 62 to pivot arm 74, through pivot point 82. The springs can extend along both sides of the pivot drive member 62 or along just one side. The translating motion of the upper end of pivot arm 74, results in a hammering-type action of the workpiece (brushhead) 86 against a surface, such as a tooth, producing cleansing thereof.

Figure 5:
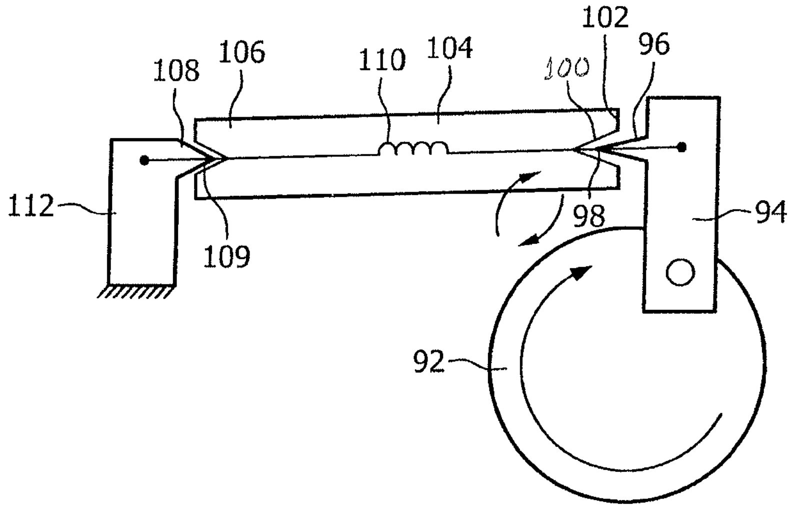
FIG. 5 is a simplified elevational view of an alternative rotational mechanical system embodiment.

FIG. 5 shows a variation of the embodiment of FIGS. 1-3. FIG. 5 also includes a rotating disc 92 driven by a DC motor (not shown), and a pivot drive member 94. Near the upper end of pivot drive member 94 is a projection 96 which terminates in a knife edge tip 98. Knife edge tip 98 makes pivoting contact with an internal end of a socket 100 located in one end 102 of a pivot arm 104. The other end 106 of pivot arm 104 includes a socket 109 into which fits a projection 108 extending from pivot member 112, which is fixed to ground. A workpiece arm at the end of which is a workpiece (not shown), such as a brushhead, extends outwardly (into the page) from the vicinity of one end 102 of pivot arm 104. A preload force is produced by a spring 110 which extends from pivot drive member 94 at one end to pivot member 112 at the other end.

The rotation of disc 92 produces an up/down, slightly arcuate motion of the one end 102 of pivot arm 104 and hence an arcuate motion of the workpiece arm and the workpiece at the free end thereof. The brush arm extends into the page for FIG. 5. Again, while the contact between the pivot drive member and the pivot arm, and between the pivot arm and the pivot member are pivoting-type connections, it should be understood that the connections could be rolling-type connections, or other types of moving connections.

Hence, an interface for rotating/pivoting parts of a mechanical system is shown which includes a preload force which extends through the axis of rotation of the interface between the parts. This preload force, which produces no torque, results in a low-friction, low-loss and low noise interface which is advantageous in many mechanical systems, particularly those which have a large number of actual uses during their lifetimes, such as a power toothbrush or shaver, among others.

Although a preferred embodiment has been disclosed for purposes of illustration, it should be understood that various changes and modifications and substitutions could be made in the preferred embodiment without departing from the spirit of the invention as defined by the claims which follow:

The invention claimed is:

1. A mechanical system for a personal care appliance, including an interface between moving parts therein, comprising:

a driving assembly including a pivot drive member;

a driven assembly including a pivot arm, which includes a workpiece assembly for use in a personal care appliance; and a mechanical joint connecting the pivot drive member to the pivot arm, including a preload assembly connected between the pivot drive member and the pivot arm providing a preload force on the joint through the axis of rotation of the joint.

2. The mechanical system of claim 1, wherein the driving assembly includes a DC motor having a motor output shaft, a rotating disc connected to the output shaft, and a drive arm connected at one end to said disc and the other end to said mechanical joint wherein the preload assembly extends along the drive arm through the axis of rotation at the mechanical joint.

3. The mechanical system of claim 2, wherein the drive arm includes a pivoting or rolling edge at the other end thereof, engaging a mating socket in a pivot arm portion of the driven assembly, wherein the engagement of the drive arm and the pivot arm define the mechanical joint.

4. The mechanical system of claim 3, wherein the preload assembly includes at least one spring to produce the preload force at the mechanical joint.

5. The mechanical system of claim 4, wherein the pivot arm is elongated, with said mating socket being positioned approximately mid length thereof and a pivot connection at one end thereof in line with the longitudinal axis of the pivot arm, engaging a fixed member grounded to a handle portion of the appliance, and wherein the workpiece is positioned at the other end of the pivot arm, moving with a generally translational motion in operation of the appliance.

6. The mechanical system of claim 3, wherein the pivot arm is elongated, having said mating socket in the vicinity of one end thereof and a pivot or rolling connection at the other end thereof to a fixed member grounded to a handle portion of the appliance.

7. The mechanical system of claim 6, wherein the workpiece assembly includes a workpiece arm extending from the pivot arm and a workpiece positioned at the end of said workpiece arm.

8. The mechanical system of claim 7, wherein the mechanical system is a power toothbrush and the workpiece is a brushhead.

9. The mechanical system of claim 8, wherein in operation the workpiece moves with an arcuate motion through an angle in the range of ±15° about a neutral position.

10. The mechanical system of claim 3, wherein the drive arm has a knife or wedge shape at the other end thereof and the mating socket in the pivot arm is configured to receive said knife or wedge-shaped drive arm in a pivoting relationship.

11. The mechanical system of claim 3, wherein the other end of the drive arm is cone shaped, and the mating socket in the pivot arm is configured to receive the cone shaped drive arm in a pivoting relationship.

12. The mechanical system of claim 3, wherein the other end of the drive arm is ball shaped, and the mating socket in the pivot arm is configured to receive the ball shaped drive arm in a rolling relationship.

13. The mechanical system of claim 4, wherein the drive arm includes a projection at the other end thereof which mates with a socket in one end surface of the pivot arm, and wherein the mechanical system includes a grounded member in the vicinity of the other end of the pivot arm which includes a projection which mates with a corresponding socket in the other end surface of the pivot arm, and wherein the preload spring connects the drive arm to the grounded member through the axis of rotation between the drive arm and the pivot arm.

* * * * *